US010144683B2

(12) United States Patent
Rachi et al.

(10) Patent No.: US 10,144,683 B2
(45) Date of Patent: *Dec. 4, 2018

(54) METHOD FOR COLLECTING ISOPRENE CONTAINED IN FERMENTED GAS, AND METHOD FOR PRODUCING PURIFIED ISOPRENE (71) Applicant: AJINOMOTO CO., INC., Tokyo (JP)

(72) Inventors: Hiroaki Rachi, Kanagawa (JP); Hiromoto Watanabe, Kanagawa (JP); Yosuke Nishio, Kanagawa (JP); Keiji Takita, Kanagawa (JP); Satoshi Hioki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/867,179

(22) Filed: Sep. 28, 2015

(65) Prior Publication Data

US 2016/0016867 A1    Jan. 21, 2016

Related U.S. Application Data (63) Continuation of application No. PCT/JP2014/057869, filed on Mar. 20, 2014.

(30) Foreign Application Priority Data

Mar. 29, 2013  (JP) ................... 2013-074262

(51) Int. Cl.
*C07C 7/12* (2006.01)
*C12P 5/00* (2006.01)
*C07C 7/00* (2006.01)
*C07C 7/13* (2006.01)
*B01D 53/047* (2006.01)

(52) U.S. Cl.
CPC .............. *C07C 7/12* (2013.01); *B01D 53/047* (2013.01); *C07C 7/005* (2013.01); *C07C 7/13* (2013.01); *C12P 5/007* (2013.01); *B01D 2253/106* (2013.01); *B01D 2257/7022* (2013.01); *B01D 2259/402* (2013.01); *Y02E 50/343* (2013.01)

(58) Field of Classification Search
CPC ........... C07C 11/18; C07C 7/005; C07C 7/12; C07C 7/13; B01D 2253/106; B01D 2257/7022; B01D 2259/402; B01D 53/047; C08G 18/2027; C08G 18/3206; C08G 2101/00; C08G 77/46; C08J 2201/22; C08J 2203/162; C08J 2205/46; C08J 2205/52; C08J 2205/10; C08J 2375/04; C08J 2383/12; C08J 2483/12; C08J 9/0028; C08J 9/0061; C08J 9/144; C12P 5/007; Y02E 50/43
See application file for complete search history.

(56) References Cited

U.S. PATENT DOCUMENTS

| | | | | |
|---|---|---|---|---|
| 3,831,346 A | * | 8/1974 | Sharp ................. | B01D 11/0426 568/621 |
| 3,977,845 A | * | 8/1976 | Walter ................. | B01D 53/047 95/100 |
| 4,570,029 A | * | 2/1986 | Kulprathipanja ........ | C07C 7/12 585/826 |
| 5,487,917 A | * | 1/1996 | Gadkaree ............ | C03C 23/0095 427/228 |
| 5,849,970 A | | 12/1998 | Fall et al. | |
| 7,041,616 B1 | | 5/2006 | Nenoff et al. | |
| 7,179,324 B2 | | 2/2007 | Baksh et al. | |
| 2006/0048562 A1 | * | 3/2006 | Oishi ................. | G01N 33/0011 73/23.2 |
| 2010/0167371 A1 | * | 7/2010 | Chotani ................. | C12P 5/026 435/167 |
| 2010/0212493 A1 | * | 8/2010 | Rasmussen ............ | B01D 53/04 95/45 |
| 2011/0046422 A1 | * | 2/2011 | McAuliffe ................ | C10L 1/04 585/16 |
| 2011/0195472 A1 | * | 8/2011 | Calabria ................. | C12P 5/007 435/167 |
| 2013/0123559 A1 | * | 5/2013 | Milam ................... | C07C 7/005 585/802 |
| 2014/0114111 A1 | | 4/2014 | Dorato et al. | |

FOREIGN PATENT DOCUMENTS

| | | |
|---|---|---|
| CN | 102906268 | 1/2013 |
| CN | 102906269 | 1/2013 |
| JP | 2004-67946 | 3/2004 |
| JP | 2004-067946 | 3/2004 |
| JP | 2004-323455 | 11/2004 |
| JP | 2007-537867 | 12/2007 |
| RU | 2010 128 902 A | 1/2012 |
| WO | WO 2009/076676 A2 | 6/2009 |
| WO | WO 2010/099550 | 9/2010 |

(Continued)

OTHER PUBLICATIONS

Whited et al. Industrial Biotechnol. (2010) 6(3): 152-163 (Year: 2010).*
International Search Report dated Jun. 17, 2014, in PCT/JP2014/057869.
Extended European Search Report dated Oct. 17, 2016 in Patent Application No. 14772798.6.
Office Action dated Jul. 26, 2017, in corresponding Chinese Patent Application No. 201480018715.8 (with English translation).
Office Action dated Nov. 7, 2017, in corresponding Japanese Patent Application No. 2015-508432 (with English-language Translation).
Office Action dated Nov. 15, 2017 in Russian Patent application No. 2015146053 with English translation, 13 pages.

(Continued)

*Primary Examiner* — Susan M Hanley
(74) *Attorney, Agent, or Firm* — Oblon, McClelland, Maier & Neustadt, L.L.P.

(57) ABSTRACT

Methods include contacting a fermented gas including isoprene with a porous adsorbent and desorbing isoprene adsorbed on the porous adsorbent. The fermented gas may be obtained by culturing a microorganism having an ability to produce isoprene.

20 Claims, 4 Drawing Sheets (56) References Cited

FOREIGN PATENT DOCUMENTS

| | | |
|---|---|---|
| WO | WO 2010/101855 | 9/2010 |
| WO | WO 2011/075534 | 6/2011 |
| WO | WO 2011/079314 | 6/2011 |
| WO | WO 2012/088462 | 6/2012 |
| WO | WO 2012/143341 | 10/2012 |

* cited by examiner

METHOD FOR COLLECTING ISOPRENE CONTAINED IN FERMENTED GAS, AND METHOD FOR PRODUCING PURIFIED ISOPRENE

CROSS-REFERENCE TO RELATED APPLICATIONS

This application is a continuation of International Patent Application No. PCT/JP2014/057869, filed on Mar. 20, 2014, the disclosure of which is incorporated herein by reference in its entirety. This application claims priority to Japanese Patent Application No. 2013-074262, filed on Mar. 29, 2013, the disclosure of which is incorporated herein by reference in its entirety.

BACKGROUND

Various exemplary embodiments of the present invention relate to methods for recovering isoprene from a fermented gas and methods for producing purified isoprene.

Fermentation is a known method for producing isoprene. Production of isoprene by the fermentation method can be carried out by culturing a microorganism having an ability to produce isoprene, such as *Bacillus subtilis*, as described in U.S. Pat. No. 5,849,970. Isoprene is volatile and has a low solubility in water—0.6 g/L. Thus, isoprene is not a product that accumulates in a culture broth, but instead is present in a fermented gas.

As a unit operation for recovering isoprene from a fermented gas, an absorption method has been known. The absorption method generally includes: i) introducing a fermented gas into an absorption tower and contacting the fermented gas and an absorption solvent so that the isoprene in the fermented gas is absorbed into the absorption solvent, ii) discharging the fermented gas, after contacting the absorption solvent, from the top part of the absorption tower, iii) flash-evaporating the absorption solvent, which has absorbed isoprene, in a vacuum container to recover isoprene, and iv) returning the absorption solvent, after recovery of isoprene, to the absorption tower and using the recycled absorption solvent. Absorption solvents used to recover isoprene in the absorption method have included an isoparaffinic solvent, as described in WO2011/075534 and WO2010/099550, and a hydrocarbon solvent having a 6 to 10 carbon atoms, as described in WO2012/143341.

Cooling is a further known technique of recovering isoprene from a fermented gas. For example, WO2010/101855 proposes a method for liquefying and recovering isoprene by cooling a fermented gas to −35° C. or less.

SUMMARY

In the production of isoprene by the fermentation method, an isoprene concentration of the fermented gas is usually 50% by volume or less, which is a low concentration. Consequently, when isoprene in the fermented gas is recovered by the absorption method, a recovery rate of isoprene relative to the amount of energy input to the process is an issue. Particularly, the isoprene concentration of the gas discharged from the top part of the absorption tower is determined by the degree of vacuum of the vacuum container. For this reason, a degree of vacuum of about 25 mmHg, for example, causes a dissipated loss from the absorption tower. The degree of vacuum in the vacuum container may be required to be set to 7 mmHg or less, for example, to provide about 1% by volume of the isoprene concentration of the discharged gas. Particularly, the degree of vacuum may be required to be set to 2 mmHg or less in view of the resistance loss of the absorption solvent flowing in pipes. However, when the absorption method is carried out under such a vacuum, a portion of the absorption solvent evaporates and thus cannot be recycled. Further, it may be difficult to obtain a vacuum pump that can achieve a high vacuum of 2 mmHg and permit treatment of large amounts of discharged gas (for example, 100 $m^3$/hour to 2000 $m^3$/hour). Consequently, by the absorption method, it is difficult to recover isoprene as a target substance while controlling the isoprene concentration of the discharged gas to be 1% by volume or less.

In addition, isoprene, which is a diene, is known to have poor heat stability. Isoprene may decompose depending on the tower temperature of a stripping tower (regeneration tower). This may further adversely affect the recovery rate of isoprene.

Recovery of isoprene in the fermented gas by the cooling method has several problems. At the time of liquefying and recovering isoprene by cooling the fermented gas, isoprene does not liquefy until the temperature reaches the condensation point of isoprene or lower. Therefore, in order to liquefy and recover isoprene in a fermented gas that has an isoprene concentration of 50% by volume or less, the cooling temperature is required to be lowered or pressure is required to be applied. Thus, the recovery rate of isoprene relative to the energy input to the process is an issue with the cooling method as well. For example, under atmospheric pressure, the temperature must be lowered to −64° C. to recover isoprene in a fermented gas that has an isoprene concentration of 50% by volume at a recovery rate of 99%. The temperature is required to be lowered to −80° C. to recover isoprene in a fermented gas that has an isoprene concentration of 10% by volume at a recovery rate of 99%. However, carbon dioxide contained in the fermented gas is turned into dry ice by cooling the fermented gas to −57° C. or less. This dry ice may clog a cooling pipe. Even under a pressure of 1 MPa, the temperature is required to be lowered to −55° C. to recover isoprene in the fermented gas that has an isoprene concentration of 10% by volume at a recovery rate of 99%. With respect to the cooling medium, methyl chloride can be used as the cooling medium when the cooling temperature is about −70° C. This cooling medium, however, is toxic to the human body and thus has not generally been used in recent years. A suitable cooling medium for industrial use, other than methyl chloride, is unknown.

In view of the foregoing, there is room for improved techniques for recovering isoprene from a fermented gas. A technique that can effectively and safely recover isoprene in a fermented gas at a high recovery rate remains desired.

An object of embodiments of the present invention is to provide a technique by which isoprene can be effectively recovered from a fermented gas at a high recovery rate.

The inventors of the present invention have intensively studied the problems described above. As a result, the inventors of the present invention have found that the problems can be solved by, for example, by performing adsorption and desorption of isoprene with a porous adsorbent.

Accordingly, the following are among exemplary embodiments of the present invention.

[1] A method for recovering isoprene in a fermented gas, the method comprising the steps of:

(I-1) contacting the fermented gas containing isoprene obtained by culturing a microorganism having an ability to produce isoprene with a porous adsorbent; and (I-2) desorbing isoprene adsorbed on the porous adsorbent.

[2] The method according to [1], further comprising the step of:

(I-3) recovering liquid isoprene by cooling the desorbed isoprene.

[3] The method according to [1] or [2], wherein the porous adsorbent is a hydrophobidized porous adsorbent.

[4] The method according to any of [1] to [3], wherein the porous adsorbent is a silica gel.

[5] The method according to any of [1] to [4], wherein the porous adsorbent has an average pore size of 100 angstroms or less.

[6] The method according to any of [1] to [5], wherein the microorganism having an ability to produce isoprene is a bacterium of the genus *Pantoea*.

[7] The method according to any of [1] to [6], wherein the isoprene is desorbed at 100° C. or less in the step (I-2).

[8] The method according to any of [1] to [7], wherein the method is carried out by a pressure swing adsorption method.

[9] The method according to [8], wherein a pressure (PI-1) in carrying out the step (I-1) and a pressure (PI-2) in carrying out the step (I-2) satisfy PI-1-PI-2≥50 kPa.

[10] The method according to [8] or [9], wherein the step (I-1) and the step (I-2) are alternately repeated.

[11] The method according to any of [1] to [10], wherein the fermented gas containing isoprene is dehydrated before the step (I-1).

[12] The method according to any of [1] to [11], wherein a treatment of removing an organic substance from the fermented gas containing isoprene is carried out before the step (I-1).

[13] The method according to any of [1] to [12], further comprising the step of:

(I-1a) discharging the fermented gas having an isoprene concentration of 0.8 C0 or less, where C0 is an isoprene concentration of the fermented gas provided to the step (I-1).

[14] A method for producing purified isoprene, the method comprising steps of:

(II-1) culturing a microorganism having an ability to produce isoprene to obtain a fermented gas containing isoprene;

(II-2) contacting the fermented gas containing isoprene with a porous adsorbent; and (II-3) desorbing isoprene adsorbed on the porous adsorbent.

[15] The method according to [14], further comprising the step of:

(II-4) recovering liquid isoprene by cooling the desorbed isoprene.

In various exemplary embodiments of methods according to the present invention, isoprene can be effectively recovered from a fermented gas at a high recovery rate.

BRIEF DESCRIPTION OF FIGURES

A more complete appreciation of the invention and many of the attendant advantages thereof will be readily obtained as the same become better understood by reference to the following detailed description when considered in connection with the accompanying drawings, wherein.

DETAILED DESCRIPTION

Hereinafter, the present invention will be described in detail with reference to exemplary embodiments.

Method for Recovering Isoprene in Fermented Gas

In various exemplary embodiments, a method for recovering isoprene in a fermented gas according to the present invention includes the following steps (I-1) and (I-2):

(I-1) contacting the fermented gas containing isoprene obtained by culturing a microorganism having an ability to produce isoprene with a porous adsorbent; and (I-2) desorbing isoprene adsorbed on the porous adsorbent.

In embodiments, a technique that adsorbs and separates specific components in mixed gas using an adsorbent is used for the purpose of reducing the emission of volatile organic compounds having a diluted concentration into the atmosphere as an environmental protection measure. It has been found that isoprene in the fermented gas is adsorbed to the porous adsorbent using such an adsorption technique, and thereafter, the isoprene adsorbed to the porous adsorbent is desorbed in a gas state without decomposing isoprene. Thus, isoprene can be effectively recovered from the fermented gas at a high recovery rate.

Step (I-1)

In embodiments, in step (I-1), the fermented gas containing isoprene obtained by culturing a microorganism having an ability to produce isoprene is contacted with a porous adsorbent.

Here, the "microorganism having an ability to produce isoprene" includes both 1) microorganisms innately able to produce isoprene, and 2) microorganisms not innately able to produce isoprene or substantially not innately able to produce isoprene but posteriori obtaining an ability to produce isoprene by introducing an isoprene synthase gene by genetic modification.

As the microorganism innately having an ability to produce isoprene, a bacterium is preferable and a bacterium of the genus *Bacillus*, a bacterium of the genus *Streptomyces*, a bacterium of the genus *Pseudomonas* are more preferable, and the bacterium of the genus *Bacillus* is further preferable. Examples of the bacterium of the genus *Bacillus* may include *Bacillus subtilis*, *Bacillus amyloliquefaciens*, and *Bacillus cereus*. Among them, *Bacillus subtilis* is preferable.

As the microorganism not innately able to produce isoprene or substantially not innately able to produce isoprene but posteriori obtaining an ability to produce isoprene by introducing isoprene synthase gene by genetic modification, a bacterium and a fungus are preferable. Examples of the bacterium may include a bacterium of the genus *Escherichia*, a bacterium of the genus *Pantoea*, a bacterium of the genus *Corynebacterium*, a bacterium of the genus *Enterobacter*, and a bacterium of the genus *Clostridium*. The bacterium of the genus *Escherichia*, the bacterium of the genus *Pantoea*, the bacterium of the genus *Corynebacterium*, and the bacterium of the genus *Enterobacter* are preferable, and the bacterium of the genus *Pantoea* is more preferable. Examples of the bacterium of the genus *Pantoea* may include *Pantoea ananatis, Pantoea stewartii, Pantoea agglomerans*, and *Pantoea citrea*. Examples of the fungus may include a fungus of the genus *Saccharomyces*, a fungus of the genus *Schizosaccharomyces*, a fungus of the genus *Yarrowia*, a fungus of the genus *Trichoderma*, a fungus of the genus *Aspergillus*, a fungus of the genus *Fusarium*, and a fungus of the genus *Mucor*. The fungus of the genus *Saccharomyces* is preferable.

A culture medium for culturing the microorganism preferably contains a carbon source because the carbon source is converted into isoprene. Examples of the carbon source may include carbohydrates such as monosaccharides, disaccharides, oligosaccharides, and polysaccharides; invert sugars made by hydrolyzing sucrose; glycerol; compounds having one carbon atom such as methanol, formaldehyde, formic acid salts, carbon monoxide, and carbon dioxide; oils such as corn oil, palm oil, and soybean oil; acetates; animal fats; animal oils; fatty acids such as saturated fatty acids and unsaturated fatty acids; lipids; phospholipids; glycerolipids; glycerol fatty acid esters such as monoglycerides, diglycerides, and triglycerides; polypeptides such as microbial proteins and vegetable proteins; renewable carbon sources such as hydrolyzed biomass carbon sources; yeast extract; and combinations thereof. The culture medium preferably contains nitrogen sources, inorganic ions, and optionally other organic trace components in addition to the carbon sources. As such nitrogen sources, inorganic ions, and other organic trace components, conventionally known optional components may be used. The culture medium may be a natural culture medium or a synthetic culture medium.

The culture conditions are not particularly limited as long as the conditions are suitable for producing isoprene, and standard cell culture conditions may be used. The culture temperature is preferably 20° C. to 37° C. The culture is preferably carried out under aerobic conditions, anoxic conditions, or anaerobiotic conditions depending on the characteristics of the microorganisms.

As a culture method, known fermentation methods such as a batch culture method, a feeding culture method, and a continuous culture method may be used.

Generally, the fermented gas obtained by culturing the microorganism having an ability to produce isoprene contains isoprene in a concentration of 50% by volume or less relative to the entire fermented gas. The isoprene concentration of the fermented gas varies depending on the type of the microorganisms, culture conditions, the amount of gas which is a carrier described below, and the like. The concentration of isoprene may be 40% by volume or less, 30% by volume or less, 20% by volume or less, or 10% by volume or less relative to the entire fermented gas. According to the present invention, even when the fermented gas having an isoprene concentration of 10% by volume or less, which is an extremely low concentration, is used, isoprene can be effectively recovered at a high recovery rate. The lower limit of the isoprene concentration of the fermented gas is usually more than 0.05%, for example, 0.1% by volume or more, 1% by volume or more, 2% by volume or more, or 3% by volume or more.

The fermented gas obtained by culturing the microorganism having an ability to produce isoprene usually contains carbon dioxide, moisture, oxygen-containing organic compounds (for example, lower alcohols, lower aldehydes, and lower fatty acids), and the like in addition to isoprene. Here "lower" means that the number of carbon atoms is in a range of 1 to 6. Specific examples of the oxygen-containing organic compounds may include one or more of organic acids (for example, acetic acid, pyruvic acid, citric acid, succinic acid, fumaric acid, malic acid, lactic acid, α-ketoglutaric acid, and formic acid), 1,3-butanediol, 2,3-butanediol, acetoin, butanol, ethanol, and methanol.

The fermented gas obtained by culturing the microorganism having an ability to produce isoprene may be used in the step (I-1) after mixing with one or more of nitrogen, air, carbon dioxide, oxygen, isoprene gas, and the like, as a carrier gas. In such a case, the "fermented gas containing isoprene" may contain one or more carrier gases in addition to the components described above.

The porous adsorbent used in the step (I-1) is preferably a hydrophobidized porous adsorbent from the viewpoint of recovering isoprene in the fermented gas at a high recovery rate. Examples of the hydrophobidized porous adsorbent may include 1) a porous adsorbent which has a surface treated with a surface treatment agent having a hydrophobic group and 2) a porous adsorbent to which hydrophobicity is conferred by thermal treatment at high temperature (for example, 200° C. or more, preferably 300° C. or more, and more preferably 400° C. or more). When zeolite is used as the porous adsorbent, zeolite in which a Si/Al atom rate is increased to 10 or more, 15 or more, 20 or more, 25 or more, or 30 or more by known a dealumination treatment such as steaming is also preferred as the hydrophobidized porous adsorbent. In such a case, the upper limit of the Si/Al atom ratio is not particularly limited. Usually, the Si/Al atom ratio may be set to 1000 or less, 500 or less, or the like.

The surface treatment agent having hydrophobic groups is not particularly limited as long as the hydrophobic group can be introduced to the surface of the porous adsorbent. Examples of the surface treatment agent may include a silane coupling agent having hydrophobic groups and a disilazane compound having hydrophobic groups. Here, examples of the hydrophobic group may include an alkyl group having 1 to 20 carbon atoms (preferably 1 to 10, more preferably 1 to 6, and further preferably 1 to 4), an aryl group having 6 to 20 carbon atoms (preferably 6 to 14, more preferably 6 to 12, and further preferably 6 to 10), and a vinyl group.

As the silane coupling agent having hydrophobic groups, a silane coupling agent having 2 or 3 hydrophobic groups is preferable. Examples of the silane coupling agent having hydrophobic groups may include trialkyl halosilanes, dialkyl halosilanes, triaryl halosilanes, diaryl halosilanes, trialkyl alkoxysilanes, dialkyl alkoxysilanes, triaryl alkoxysilanes, and diaryl alkoxysilanes. Here, the numbers of carbon atoms of the alkyl group and the aryl group are the same as described above. A chlorine atom is preferable as the halogen atom.

Specific examples of the preferred silane coupling agent having hydrophobic groups may include trimethylchlorosilane, trimethylmethoxysilane, triphenylchlorosilane, and triphenylmethoxysilane.

As the disilazane compound having hydrophobic groups, a disilazane compound having 4, 5, or 6 hydrophobic groups is preferable. Examples of the disilazane compound having hydrophobic groups may include hexaalkyldisilazane, pentaalkyldisilazane, tetraalkyldisilazane, hexaaryidisilazane, pentaaryidisilazane, and tetraaryldisilazane. Here, the numbers of carbon atoms of the alkyl group and the aryl group are the same as described above. Specific examples of the preferred disilazane compound having hydrophobic groups may include hexamethyldisilazane, hexaphenyldisilazane, pentamethyldisilazane, pentaphenyldisilazane, tetraphenyldisilazane, and tetraphenyldisilazane.

The average pore size of the porous adsorbent is preferably 100 angstroms or less, more preferably 80 angstroms or less, and further preferably 60 angstroms or less from the viewpoint of recovering isoprene in the fermented gas at a high recovery rate. The lower limit of the average pore size of the porous adsorbent is usually 2 angstroms or more, preferably 3 angstroms or more, 4 angstroms or more, 5 angstroms or more, or 20 angstroms or more.

The average pore size of the porous adsorbent can be measured by known methods such as a gas adsorption method and a small angle X-ray scattering method.

As the porous adsorbent, a zeolite or a silica gel are preferable and the silica gel is particularly preferable from the viewpoint of recovering isoprene in the fermented gas at a high recovery rate.

The porous adsorbent may be used singly or in a combination of two or more porous absorbents. When two or more porous adsorbents are used, the porous adsorbents may mixed or the porous adsorbents may stacked to form separate layers of each type of porous adsorbent.

In the step (I-1), conditions under which the fermented gas containing isoprene is contacted with the porous adsorbent are not particularly limited as long as isoprene is smoothly adsorbed to the porous adsorbent.

In one embodiment, the temperature when the fermented gas containing isoprene is contacted with the porous adsorbent is preferably 50° C. or less, more preferably 40° C. or less, and further preferably 30° C. or less. The lower limit of the temperature is not particularly limited. The lower limit is usually 0° C. or more and preferably 10° C. or more.

In one embodiment, the linear velocity of the fermented gas when the fermented gas containing isoprene is contacted with the porous adsorbent is preferably in a range of 0.5 cm/sec to 300 cm/sec, more preferably in a range of 0.8 cm/sec to 300 cm/sec, and further preferably in a range of 1.0 cm/sec to 300 cm/sec, in a range of 5 cm/sec to 300 cm/sec, in a range of 10 cm/sec to 300 cm/sec, or in a range of 10 cm/sec to 200 cm/sec.

The pressure when the fermented gas containing isoprene is contacted with the porous adsorbent is not particularly limited as long as isoprene in the fermented gas is adsorbed to the porous adsorbent. From the viewpoint of recovering isoprene in the fermented gas at a high recovery rate, it is preferable that the pressure in the step (I-1) be higher than that in the step (I-2) described below. Exemplary detailed pressure conditions will be described below.

The time when the fermented gas containing isoprene is contacted with the porous adsorbent may be appropriately determined depending on the contact conditions such as the isoprene concentration of the fermented gas, the type of the porous adsorbent, the temperature, the pressure, and the linear velocity. In embodiments, a breakthrough time is measured ahead of time and such breakthrough time is preferably set as the upper limit of the contact time. Here, the "breakthrough time" means a time until the porous adsorbent reaches saturated adsorption.

In the step (I-1), after contacting the porous adsorbent, the fermented gas is discharged out of the system. In embodiments of the present invention, isoprene in the fermented gas can be adsorbed to the porous adsorbent at a high adsorption rate in the step (I-1) and the isoprene concentration of the fermented gas after contacting the porous adsorbent is extremely low. The isoprene concentration of the fermented gas after contacting the porous adsorbent, depending on the isoprene concentration of the fermented gas introduced to the step (I-1), is usually 1% by volume or less or 0.1% by volume or less, preferably 500 ppm or less, more preferably 100 ppm or less, and further preferably 50 ppm or less, and further more preferably 10 ppm or less.

When the isoprene concentration of the fermented gas introduced to the step (I-1) (that is, the fermented gas before contacting the porous adsorbent) is defined as C0 and the isoprene concentration of the fermented gas after contacting the porous adsorbent in the step (I-1) is defined as C1, C0 and C1 satisfy C1<C0. The C1/C0 ratio is usually 0.8 or less, preferably 0.6 or less, more preferably 0.4 or less, further preferably 0.2 or less, and further more preferably 0.1 or less, 0.01 or less, or 0.001 or less.

In one preferred embodiment, the method for recovering isoprene in a fermented gas according to the present invention may further include the following step (I-1a) after the step (I-1):

(I-1a) discharging the fermented gas having an isoprene concentration of 0.8 C0 or less, where C0 is an isoprene concentration of the fermented gas provided to the step (I-1).

In the step (I-1a), the isoprene concentration of the discharged fermented gas is preferably 0.6 C0 or less, more preferably 0.4 C0 or less, further preferably 0.2 C0 or less, and further more preferably 0.1 C0 or less, 0.01 C0 or less, or 0.001 C0 or less, where the isoprene concentration of the fermented gas introduced to the step (I-1) is defined to C0.

In one preferred embodiment, the step (I-1a) may be the step (I-1a'):

(I-1a') discharging the fermented gas having an isoprene concentration of 1% by volume or less.

In the step (I-1a'), the isoprene concentration of the discharged fermented gas is preferably 0.1% by volume, more preferably 500 ppm or less, further preferably 100 ppm or less, further more preferably 50 ppm or less, and particular preferably 10 ppm or less.

Step (I-2)

In embodiments, in the step (I-2), the isoprene adsorbed to the porous adsorbent is desorbed, and isoprene is recovered.

Generally, methods for desorbing a target substance from an adsorbent significantly differ between a case in which the desorbed target substance is used in another process and a case in which the desorbed target substance is not used in another process. For example, in the technique of reducing the emission of volatile organic compounds into the atmosphere described above, the adsorbed volatile organic compounds are not required to be desorbed while retaining their structures because of the purpose of the technique. Consequently, adsorbents are often revitalized by strongly heating the adsorbent to which the volatile organic compounds are adsorbed to desorb the volatile organic compounds. In such a case, the volatile organic compounds usually change their structure before and after the desorption treatment by decomposition and the like.

By contrast, an object of the present invention is to recover isoprene adsorbed to the porous adsorbent as a product, which requires reduction or prevention of structure change in the isoprene before and after the desorption treatment.

Conditions at the time of desorbing isoprene adsorbed to the porous adsorbent should be conditions in which isoprene can be desorbed while maintaining quality by reducing or preventing structural changes to isoprene.

In one embodiment, the temperature at the time of desorbing the isoprene adsorbed to the porous adsorbent is preferably 100° C. or less, more preferably 80° C. or less, and further preferably 60° C. or less. The lower limit of the temperature is not particularly limited. The lower limit is usually 0° C. or more and preferably 10° C. or more.

The step (I-2) may be carried out under the flow of purge gas. The purge gas is not particularly limited as long as the purge gas does not cause structural changes to isoprene. Examples of the purge gas may include air, nitrogen, and a mixed gas thereof. Prior to the step (I-2), the moisture in the purge gas is preferably removed. When the step (I-2) is carried out under the flow of the purge gas, the linear velocity of the purge gas is not particularly limited. The linear velocity is preferably in a range of 0.5 cm/sec to 300 cm/sec and more preferably in a range of 1.0 cm/sec to 300 cm/sec.

The pressure at the time of desorbing the isoprene adsorbed to the porous adsorbent is not particularly limited. The pressure is preferably atmospheric pressure or lower. This can reduce the amount of purge gas used when the desorption is carried out under the flow of the purge gas. From the viewpoint of recovering isoprene in the fermented gas at a high recovery rate, it is preferable that the pressure in the step (I-2) be lower than that in the step (I-1). Exemplary detailed pressure conditions will be described later.

The time for desorbing isoprene adsorbed to the porous adsorbent can be appropriately determined depending on various types of desorption conditions such as the type of the porous adsorbent, the temperature, and the pressure.

A mixed gas containing isoprene, other adsorbed substances, the purge gas when it is used, and other components may be obtained by the step (I-2). The obtained mixed gas may be cooled (for example, −20° C. to 15° C.) to condense the isoprene gas to recover liquid isoprene.

Consequently, in one preferred embodiment, the method for recovering isoprene in the fermented gas according to the present invention includes the following step (I-3) in addition to the steps (I-1) and (I-2):

(I-3) recovering liquid isoprene by cooling the desorbed isoprene.

The mixed gas after recovering the liquid isoprene may contain small amounts of isoprene and thus this mixed gas may be used in the step (I-1).

In one preferred embodiment, the method for recovering the isoprene in the fermented gas according to the present invention is carried out by a pressure swing adsorption method (hereinafter also referred to as a "PSA method"). By carrying out the PSA method, structural changes to isoprene (quality deterioration) can be further reduced and the isoprene in the fermented gas can be recovered at a high recovery rate.

When isoprene is recovered by the PSA method, the pressure (PI-1) when the step (I-1) is carried out and the pressure (PI-2) when the step (I-2) is carried out satisfy PI-1>PI-2. From the viewpoint of recovering the isoprene in the fermented gas at a high recovery rate, PI-1 and PI-2 preferably satisfy PI-1-PI-2≥50 kPa, more preferably satisfy PI-1-PI-2≥90 kPa, further preferably satisfy PI-1-PI-2≥100 kPa, even more preferably PI-1-PI-2≥150 kPa, and particularly preferably PI-1-PI-2≥200 kPa, PI-1-PI-2≥300 kPa, PI-1-PI-2≥400 kPa, PI-1-PI-2≥500 kPa, PI-1-PI-2≥600 kPa, PI-1-PI-2≥700 kPa, or PI-1-PI-2≥800 kPa. The upper limit of difference between PI-1 and PI-2 (PI-1-PI-2) is usually 900 kPa or less and preferably 800 kPa or less.

When isoprene is recovered by the PSA method, the pressure (PI-1) is not particularly limited as long as the pressure (PI-1) at the time of carrying out the step (I-1) satisfies PI-1>PI-2 as described above and may be determined depending on the adsorption capacity of the porous adsorbent used. The pressure (PI-1) is usually 950 kPaG or less and preferably 750 kPaG or less.

When the PSA method is carried out, the pressure (PI-2) is not particularly limited as long as the pressure (PI-2) at the time of carrying out the step (I-2) satisfies PI-1>PI-2 as described above and may be determined depending on the adsorption capacity of the porous adsorbent used. The pressure (PI-2) is usually 900 kPaG or less, preferably 100 kPaG or less, more preferably 0 kPaG or less, −50 kPaG or less, −90 kPaG or less, or −100 kPaG or less.

When the PSA method is carried out, the step (I-1) and the step (I-2) are preferably alternately repeated.

The switching time of the step (I-1) and the step (I-2), that is, the time from the end point of the step (I-1) to the start point of the step (I-2), or the time from the end point of the step (I-2) to the start point of the next step (I-1) is preferably 1 to 30 minutes. At the time of switching, a purge operation is preferably carried out. The purge operation is usually carried out by flowing air, nitrogen, or mixed gas thereof at normal temperature through the porous adsorbent.

Hereinafter, one embodiment in which the PSA method is carried out in a method according to the present invention will be described with reference to FIG. 1.

Figure 1:
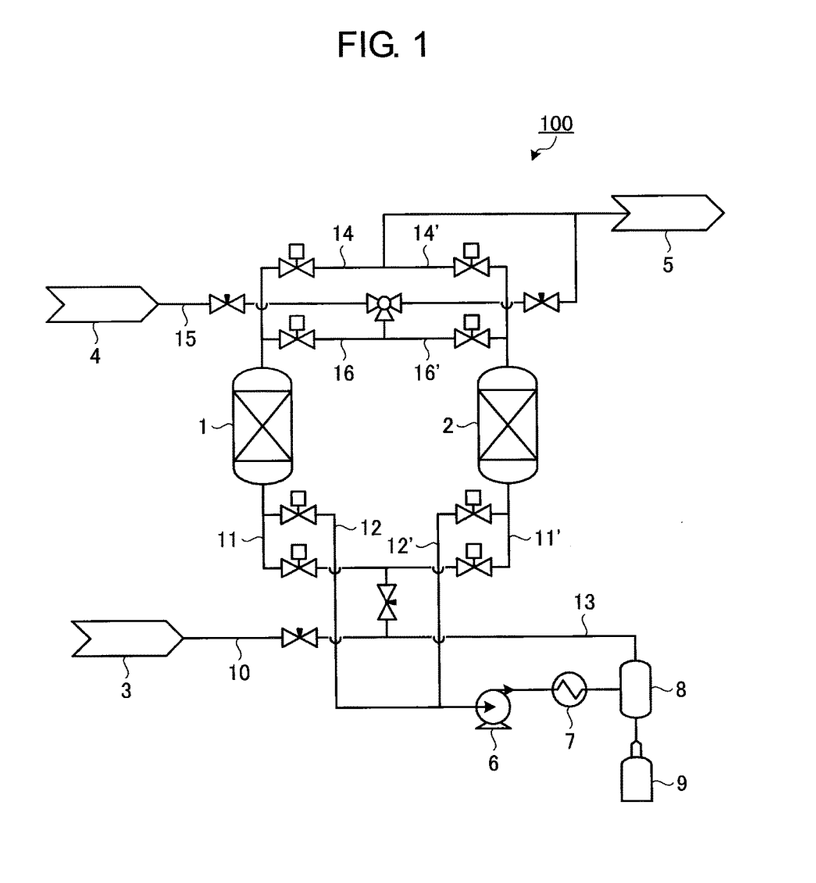
FIG. 1 is a schematic view of an exemplary embodiment of an isoprene recovery apparatus according to the present invention.

FIG. 1 illustrates an exemplary isoprene recovery apparatus 100 according to the present invention including a first adsorption tower 1 and a second adsorption tower 2. The porous adsorbent is included in the first adsorption tower 1 and the second adsorption tower 2 as a porous adsorbent layer.

First, the fermented gas containing isoprene (hereinafter, also referred to as "feed gas") 3 is supplied to the first adsorption tower 1 (or the second adsorption tower 2) through feed gas supply pipes 10 and 11 (or 10 and 11'). By this operation, the fermented gas containing isoprene is contacted with the porous adsorbent in the first adsorption tower 1 (or the second adsorption tower 2) (that is, the step (I-1)).

After the step (I-1) is carried out under certain conditions, the treated fermented gas is discharged through a discharge pipe 14 (or 14') (that is, the step (I-1a)).

Subsequently, purge gas 4 is supplied to the first adsorption tower 1 (or the second adsorption tower 2) through purge gas supply pipes 15 and 16 (or 15 and 16') and is drawn by a vacuum pump 6 through an isoprene-containing purge gas supply pipe 12 (or 12'). By this operation, isoprene adsorbed to the porous adsorbent is desorbed in the first adsorption tower 1 (or the second adsorption tower 2) (that is, the step (I-2)).

After the step (I-2) is carried out under certain conditions, the isoprene-containing purge gas is cooled with a condenser 7 to liquefy isoprene. Thereafter, the liquefied isoprene and other gas components are separated with a separator 8 to recover the liquid isoprene 9 (that is, the step (I-3)).

Isoprene remains in the gas components separated with the separator 8. Consequently, the separated gas components are returned to the feed gas supply pipe 10 through a return pipe 13. The returned separated gas components can be used in the next step (I-1) by adding it to the feed gas 3.

The isoprene in the fermented gas can be continuously recovered by operating so that at the time of carrying out the step (I-1) in the first adsorption tower 1, the step (I-2) is carried out in the second adsorption tower 2 and at the time of carrying out the step (I-2) in the first adsorption tower 1, the step (I-1) is carried out in the second adsorption tower 2.

One embodiment in which the PSA method is carried out in a method according to the present invention is described above with respect to an isoprene recovery apparatus including two adsorption towers. The number of adsorption towers included in the isoprene recovery apparatus, however, is not particularly limited. The isoprene recovery apparatus may include one adsorption tower, two adsorption towers, or three or more adsorption towers.

Other Processes

The fermented gas obtained by culturing the microorganism having an ability to produce isoprene usually contains moisture. When the fermented gas contains a large amount of moisture, e.g., saturated water vapor, the fermented gas containing isoprene is preferably dehydrated before the step (I-1) from the viewpoint of achieving a desired isoprene recovery rate.

For the dehydration of the fermented gas containing isoprene, known methods for removing moisture from gas may be used. Examples of the dehydration method may include i) a method of contacting the fermented gas containing isoprene with a moisture absorbent and ii) a method of cooling the fermented gas containing isoprene to condense and remove moisture. In the method of i), the moisture absorbent is not particularly limited. Examples of the moisture absorbent may include chemical moisture absorbents such as calcium chloride, diphosphorus pentaoxide, and anhydrous copper sulfate; and physical moisture absorbents such as silica gel, alumina gel, and zeolite. The physical moisture absorbent is preferably hydrophobically untreated. In the method of ii), the cooled temperature of the fermented gas containing isoprene is preferably 0° C. to 30° C. and more preferably 0° C. to 20° C. The cooling may be carried out by using known heat exchangers such as a coil type heat exchanger and a shell-and-tube type heat exchanger.

Figure 2:
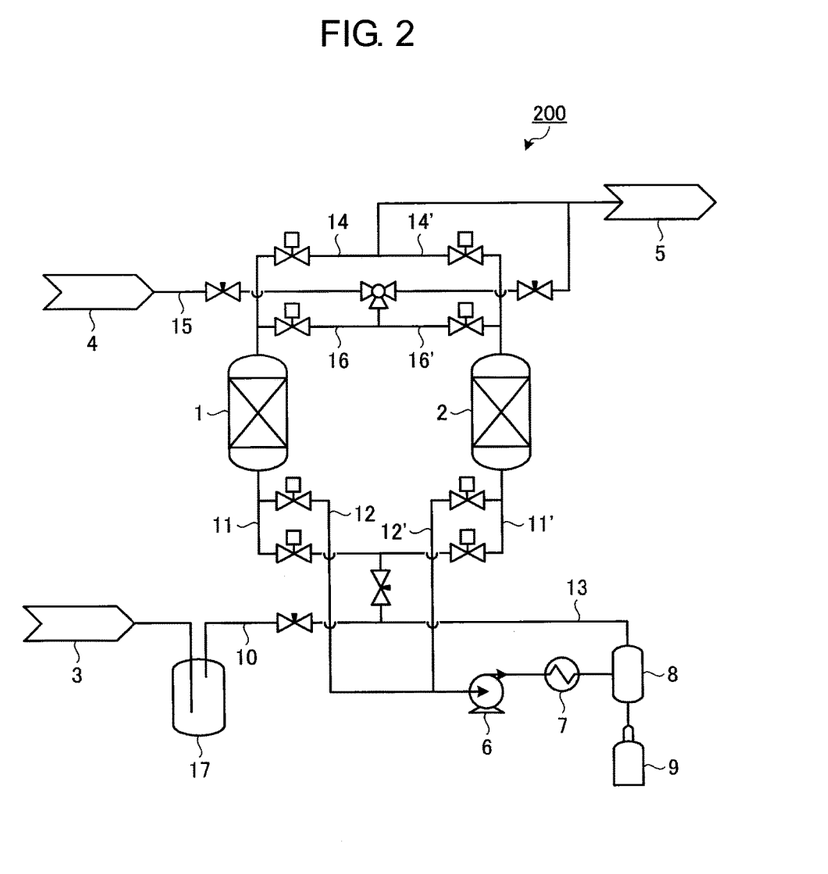
FIG. 2 is a schematic view of an exemplary embodiment of an isoprene recovery apparatus according to the present invention equipped with a dehydration treatment tank.

When the fermented gas containing isoprene is dehydrated before the step (I-1), the method of the present invention can be carried out by using, for example, the isoprene recovery apparatus 200 illustrated in FIG. 2. The isoprene recovery apparatus 200 includes a dehydration treatment tank 17 located in line of the feed gas supply pipe 10. Other constituents are the same as the constituents of the isoprene recovery apparatus 100.

A treatment to remove an organic substance (organic substance removal treatment) is preferably carried out before the step (I-1), from the viewpoint of reducing the amount of organic impurities in the recovered isoprene. The fermented gas containing isoprene is preferably washed with water or cooled as the organic substance removal treatment. However, the treatment is not limited to washing with water and cooling as long as the method can remove organic substances (particularly oxygen-containing organic compounds described above), including a method of adsorbing the organic substances to an adsorbent and absorbing the organic substances into a solution other than water.

Examples of the method of washing the fermented gas containing isoprene with water may include a method of bubbling the fermented gas containing isoprene into water and a method of dropping water from the upper part of a water washing tower such as a scrubber and aerating gas from the lower part.

The temperature of the water used in the water washing treatment is preferably 5° C. to 40° C. and more preferably 10° C. to 25° C.

When the fermented gas containing isoprene is washed with water before the step (I-1), the fermented gas containing isoprene is preferably dehydrated after this water washing. Consequently, in one preferred embodiment, the method for recovering the isoprene in the fermented gas according to the present invention includes the step of washing the fermented gas containing isoprene with water and thereafter dehydrating the gas before the step (I-1).

Figure 3:
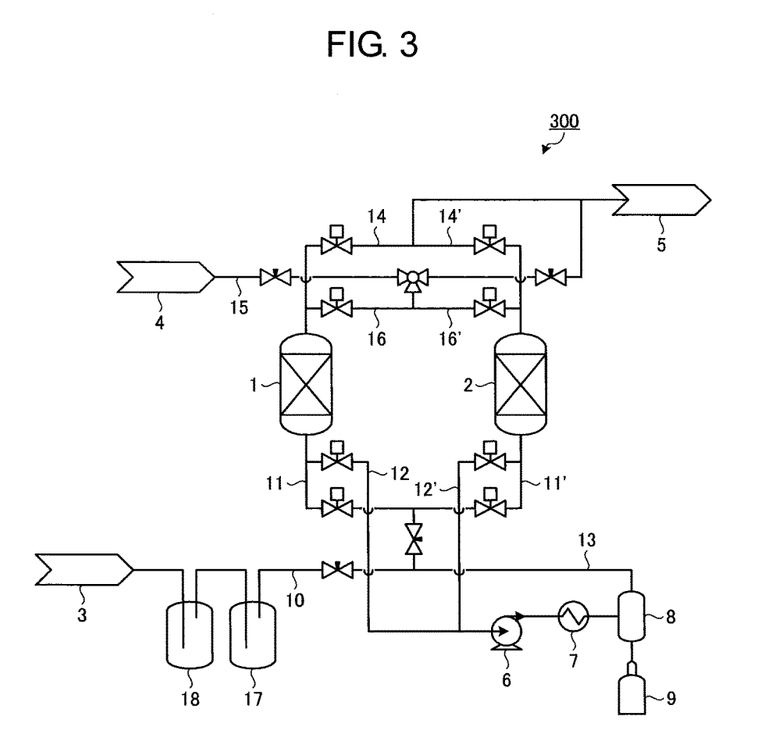
FIG. 3 is a schematic view of an exemplary embodiment of an isoprene recovery apparatus according to the present invention equipped with a water-washing treatment tank and a dehydration treatment tank.

When the treatment to remove an organic substance from the fermented gas containing isoprene is carried out before the step (I-1), the method of the present invention can be carried out by using the isoprene recovery apparatus 300 illustrated in FIG. 3. The isoprene recovery apparatus 300 includes a water-washing treatment tank 18 and the dehydration treatment tank 17 located upstream from the feed gas supply pipe 10. Other constituents are the same as the constituents of the isoprene recovery apparatus 100.

When the fermented gas containing isoprene is cooled, and the dehydration treatment and the organic substance removal treatment are carried out, the method of the present invention can be carried out by using, for example, the isoprene recovery apparatus 200 illustrated in FIG. 2. In such a case, the dehydration treatment tank 17 in the isoprene recovery apparatus 200 also has the role of a tank for the organic substance removal treatment.

In the method for recovering isoprene in the fermented gas according to the present invention, decarbonation treatment of the fermented gas containing isoprene is preferably carried out before the step (I-1). In the fermented gas obtained by culturing the microorganism having an ability to produce isoprene, a considerable amount of carbonic acid gas (carbon dioxide) is contained. By reducing the amount of the carbonic acid gas in the fermented gas, the amount of the fermented gas to be a treatment target can be reduced and energy required for heating and pressurization at the time of adsorption and desorption can be reduced.

Examples of the decarbonation treatment may include a method of washing the fermented gas containing isoprene with low temperature water and a method of washing with alkaline aqueous solution. Suitable examples of the method of washing the fermented gas containing isoprene with the low temperature water or the alkaline aqueous solution may include a method of bubbling the fermented gas containing isoprene into the low temperature water or the alkaline aqueous solution and method of dropping the low temperature water or the alkaline aqueous solution from the upper part of a water washing tower such as a scrubber and aerating the fermented gas from the lower part. The "low temperature water" used in the decarbonation treatment is water having a temperature of preferably 30° C. or less, more preferably 25° C. or less, further preferably 20° C. or less, further more preferably 15° C. or less, and particularly preferably 10° C. or less.

When the method of washing with the low temperature water is used as the decarbonation treatment, the low temperature water washing treatment may be carried out with the water washing treatment for removing the organic impurities at the same time or may be carried out as an individual treatment.

In embodiments of the method for recovering the isoprene from the fermented gas according to the present invention, the isoprene contained in the fermented gas in a low concentration of 50% by volume or less can be recovered from a large amount of the fermented gas exceeding 1000 m³/hour at a high recovery rate. In embodiments of the present invention, when the fermented gas contains isoprene in an extremely low concentration of 40% by volume, 30% by volume, 20% by volume, or 10% by volume, the isoprene can be recovered at a high recovery rate.

When the method of the present invention includes carrying out the PSA method, the isoprene concentration of the treated fermented gas discharged from the adsorption tower may be 1% by volume, which is a low concentration. This isoprene concentration can be reduced to, for example, 0.1% by volume or less, 500 ppm or less, 100 ppm or less, 50 ppm or less, or 10 ppm or less.

Method for Producing Purified Isoprene

Various exemplary embodiments of the present invention also include a method for producing purified isoprene. In embodiments, the method for producing purified isoprene according to the present invention includes the following steps (II-1), (II-2), and (II-3):

(II-1) culturing a microorganism having an ability to produce isoprene to obtain fermented gas containing isoprene;
(II-2) contacting the fermented gas containing isoprene with a porous adsorbent; and
(II-3) desorbing isoprene adsorbed on the porous adsorbent.

In the step (II-1), the microorganism having an ability to produce isoprene is cultured to obtain fermented gas containing isoprene.

The microorganism having an ability to produce isoprene, culture conditions, and the like are as described in "[Method for recovering isoprene in fermented gas]" above.

The step (II-2) and the step (II-3) may be carried out in the same manner as the step (I-1) and the step (I-2) described in "[Method for recovering isoprene in fermented gas]" above. After the step (II-2), the step (I-1a) described above may be carried out. In this case, the step (I-1a) described above can be applied by replacing the "step (I-1)" with the "step (II-2)".

The method for producing the purified isoprene according to the present invention preferably includes the following step (II-4) in addition to the steps (II-1), (II-2), and (II-3):

(II-4) recovering liquid isoprene by cooling the desorbed isoprene.

In embodiments of the method for producing purified isoprene according to the present invention, one or more treatments selected from i) a treatment to remove an organic substance from the fermented gas containing isoprene, ii) dehydrating the fermented gas containing isoprene, and iii) decarbonation treatment of the fermented gas containing isoprene may be carried out.

These treatments are as described in "[Method for recovering isoprene in fermented gas]" above.

A more complete appreciation of the invention and many of the attendant advantages thereof will be readily obtained as the same become better understood by reference to the following detailed description when considered in connection with the accompanying drawings, wherein:

EXAMPLES

In the following examples, and throughout this specification, all parts and percentages are by weight, and all temperatures are in degrees Celsius, unless expressly stated to be otherwise. Where the solids content of a dispersion or solution is reported, it expresses the weight of solids based on the total weight of the dispersion or solution, respectively. Where a molecular weight is specified, it is the molecular weight range ascribed to the product by the commercial supplier, which is identified. Generally this is believed to be weight average molecular weight.

Example 1

1. Evaluation of Porous Adsorbent 1.1. Types of Evaluated Porous Adsorbents

As the porous adsorbents, activated carbon ["Y-4" (trade name), manufactured by Ajinomoto Fine-Techno Co., Inc.], hydrophobic molecular sieves (high-silica zeolite) ["Hisiv-1000", "Hisiv-3000", and "USKY-790" (trade names), manufactured by UNION SHOWA K. K.], and hydrophobic silica gels ["S-3" and "S-6" (trade names), manufactured by Fuji Silysia Chemical Ltd.] were used. The average pore sizes of each porous adsorbent were as follows:

Activated carbon "Y-4", Approximately 20 angstroms;
Hydrophobic molecular sieve "Hisiv-1000": 9 angstroms;
Hydrophobic molecular sieve "Hisiv-3000": 6 angstroms;
Hydrophobic molecular sieve "USKY-790": 9 angstroms;
Hydrophobic silica gel "S-3": Approximately 30 angstroms; and
Hydrophobic silica gel "S-6": Approximately 60 angstroms.

1.2. Method for Preparing Isoprene Gas

To a three-neck flask warmed at 37° C., reagent isoprene (manufactured by Tokyo Kasei Kogyo Co., Ltd.) was added dropwise from one opening at a rate of 0.025 mL/min and nitrogen gas was aerated from another opening at a rate of 300 mL/min. From the remaining opening, gas having an isoprene concentration of about 1% by volume was obtained.

1.3. Measurement of Isoprene Adsorption Amount

Into a stainless steel column having an inner diameter of 2 cm and a length of 20 cm of which both ends can be sealed, the porous adsorbent was packed at the weight set forth in TABLE 1. The gas having an isoprene concentration of 1% by volume obtained in the above "1.2. Method for preparing isoprene gas" was aerated through the column in which the porous adsorbent was packed at a flow rate of 300 mL/min (a linear velocity of 1.59 cm/sec). The isoprene concentration at the outlet of the column was continuously measured with a sensor gas chromatograph ("ODSA-P2", manufactured by FIS Inc.). Occurrence of breakthrough was determined to be the time at which the isoprene concentration at the outlet of the column reached around 1% by volume, and the aeration was stopped at that time. Thereafter, the total weight of the column and the porous adsorbent was measured. The weight of the porous adsorbent was calculated by subtracting the column weight from the total weight. The increase in the weight of the porous adsorbent was determined to be the adsorbed isoprene weight. The results are set forth in TABLE 1.

TABLE 1

Isoprene adsorption amount

| Porous adsorbent | Breakthrough time (hr) | Adsorbent weight (g) | Adsorbed isoprene amount (g) | Adsorption rate* (%) |
|---|---|---|---|---|
| Activated carbon (Y-4) | 7 | 20.68 | 4.44 | 21.5 |
| Hydrophobic molecular sieve (Hisiv-1000) | 1.6 | 20.00 | 2.53 | 12.7 |
| Hydrophobic molecular sieve (Hisiv-3000) | 1.5 | 20.00 | 1.13 | 5.7 |
| Hydrophobic molecular sieve (USKY-790) | 1.5 | 20.00 | 2.24 | 11.2 |
| Hydrophobic silica gel (S-3) | 1.5 | 20.05 | 1.39 | 6.9 |
| Hydrophobic silica gel (S-6) | 1.5 | 20.04 | 0.68 | 3.4 |

*(Adsorbed isoprene amount)/(Adsorbent weight) × 100 (%)

As shown in TABLE 1, the activated carbon adsorbed the largest amount of isoprene.

1.4. Measurement of Isoprene Desorption Amount

A vacuum pump was connected to one end of the column in which the porous adsorbent was packed in "1.3. Measurement of isoprene adsorption amount" above, and the inner pressure of the column was reduced to 3.4 kPa. The column was heated to 80° C. when the activated carbon and the hydrophobic molecular sieves were used. With respect to the hydrophobic silica gels, nitrogen gas was aerated from the column opening opposite from the opening connected to the vacuum pump at a flow rate of 300 mL/min at room temperature (25° C.).

The desorption time was 7 hours in the case of the activated carbon, 16 hours or 21 hours in the cases of the hydrophobic molecular sieves, and 0.5 hours in the cases of the hydrophobic silica gels. After the desorption treatment, the total weight of the column and the porous adsorbent were measured. The weight of the porous adsorbent was calculated by subtracting the column weight from the total weight. The decrease in the weight of the porous adsorbent was determined to be the desorbed isoprene weight. The results are set forth in TABLE 2.

TABLE 2

Isoprene desorption amount

| Porous adsorbent | Desorption time (hr) | Adsorbed isoprene weight (g) | Desorbed isoprene weight (g) | Desorption rate* (%) |
|---|---|---|---|---|
| Activated carbon (Y-4) | 7 | 4.44 | 0.47 | 11 |
| Hydrophobic molecular sieve (Hisiv-1000) | 16 | 2.53 | 0.13 | 5 |
| Hydrophobic molecular sieve (Hisiv-3000) | 16 | 1.13 | 0.3 | 27 |
| Hydrophobic molecular sieve (USKY-790) | 21 | 2.24 | 0.1 | 4 |
| Hydrophobic silica gel (S-3) | 0.5 | 1.39 | 1.37 | 99 |
| Hydrophobic silica gel (S-6) | 0.5 | 0.68 | 0.69 | 101 |

*(Desorbed isoprene amount)/(Adsorbed isoprene amount) × 100 (%)

With respect to the activated carbon and the hydrophobic molecular sieves, isoprene could not be sufficiently desorbed even when the desorption operation was carried out for a long time. With respect to the hydrophobic molecular sieve (Hisiv-1000), the desorption rate was measured under conditions including flowing nitrogen gas at a flow rate of 300 mL/min, which were the same conditions as in the cases of the hydrophobic silica gels. However, the desorption rate of isoprene did not change.

On the other hand, with respect to the hydrophobic silica gels, almost all adsorbed isoprene could be desorbed in a desorption time of 0.5 hours.

Example 2

2. Recovery of Isoprene by PSA Method and Quality Evaluation of Recovered Isoprene 2.1. Description of Isoprene Recovery Apparatus and Recovery Conditions In this Example, isoprene recovery apparatus illustrated in FIG. 1, FIG. 2, or FIG. 3 was used. A two-layer structure of porous adsorbent layers using the hydrophobic silica gel "S-3" and the hydrophobic silica gel "S-6" was provided in each of the first adsorption tower 1 (inner diameter 8.4 cm) and the second adsorption tower 2 (inner diameter 8.4 cm). The hydrophobic silica gel "S-3" was used as the lower part layer in the adsorption tower (feed gas upstream layer) and the hydrophobic silica gel "S-6" was used as the upper part layer in the adsorption tower (feed gas downstream layer). The porous adsorbent layers were provided in a pre-coated state by blowing with gas having an isoprene concentration of 1% by volume.

In an adsorption step, the feed gas 3 prepared by adjusting the isoprene concentration to 1% by volume was supplied to the first adsorption tower 1 (or the second adsorption tower 2) through the feed gas supply pipes 10 and 11 (or 10 and 11'). Conditions at the time of adsorption were a temperature of 25° C., a pressure of 101.3 kPa, and a feed gas linear velocity of 0.9 cm/sec. The isoprene concentration of the discharged gas 5 emitted to the atmosphere after the adsorption step was measured with a sensor gas chromatograph ("ODSA-P2", manufactured by FIS Inc.).

In a desorption step, nitrogen gas was used as the purge gas 4 and the pressure in the adsorption tower was reduced to 3.3 kPa with the vacuum pump 6 (linear velocity of purge gas: 0.92 cm/sec). Cooling water having temperature of 4° C. was circulated in the condenser 7 to cool the purge gas containing isoprene.

The operation was carried out by alternately switching the adsorption step and the desorption step (the number of iterations of each step: 24 times; switching time of each step: 15 minutes).

2.2. Method for Preparing Feed Gas

To a three-neck flask warmed to 37° C., reagent isoprene (manufactured by Tokyo Kasei Kogyo Co., Ltd.) was added dropwise from one opening at a rate of 0.1 mL/min and nitrogen gas was aerated from another opening at a rate of 2.5 L/min. From the remaining opening, Feed Gas A (nitrogen gas carrier) containing isoprene at a concentration of about 1% by volume was obtained.

Feed Gas B (air carrier) containing isoprene at a concentration of about 1% by volume was obtained in the same manner except that air was used instead of nitrogen gas.

Feed gas containing saturated water vapor was prepared by the following procedure. Water was placed in a three-neck flask warmed to 37° C. Reagent isoprene was added dropwise from one opening at a rate of 0.1 mL/min, and air was aerated from another opening at a rate of 2.5 L/min. From the remaining opening, Feed Gas C containing isoprene at a concentration of about 1% by volume and saturated water vapor (saturated water vapor-air carrier) was obtained.

Simulated fermented gas was prepared by the following procedure. The culture broth obtained by culturing isoprene-producing bacteria (host microorganism: *Pantoea ananatis*) in a glucose culture medium described in TABLE 3 for 24 hours was placed in a three-neck flask warmed at 37° C. Reagent isoprene was added dropwise from one opening at a rate of 0.1 mL/min and air was aerated from another opening at a rate of 2.5 L/min. From the remaining opening, Feed Gas D (simulated fermented gas) containing isoprene at a concentration of about 1% by volume was obtained.

TABLE 3

| Glucose culture medium composition |  |
| --- | --- |
| A part (final concentration) |  |
| Glucose | 40 g/L |
| MgSO$_4$•7aq | 2.0 g/L |
| B part |  |
| (NH$_4$)$_2$SO$_4$ | 2.0 g/L |
| KH$_2$PO$_4$ | 2.0 g/L |
| FeSO$_4$•7aq | 20 mg/L |
| MnSO$_4$•5aq | 20 mg/L |
| Yeast Extract | 4.0 g/L |

After each of the A part and the B part described in TABLE 3 above was prepared in an amount of 50 mL, the parts were heated and sterilized at 115° C. for 10 minutes. After naturally cooling, the A part and the B part were mixed and 1.0 g of calcium carbonate was added. The mixture was used as the culture medium.

2.3. Method for Dehydrating Feed Gas

When the feed gas was dehydrated, the dehydration was carried out by the following method. 300 g of calcium chloride was filled in a glass medium bottle having a capacity of 500 mL to prepare a calcium chloride bottle. The feed gas was dehydrated by aerating the feed gas through the calcium chloride bottle at a flow rate of 2.5 L/min.

2.4. Method for Carrying out Treatment to Remove Organic Substance from Feed Gas When the organic substance removal treatment of the feed gas was carried out, the treatment was carried out by washing the feed gas with water by the following procedure. 300 mL of water was placed in a glass washing bottle having a capacity of 500 mL, and the bottle was cooled by immersing the bottle in a thermostat bath at 10° C. The feed gas was washed with water by passing the feed gas through the glass washing bottle at a flow rate of 2.5 L/min.

2.5. Recovery Results of Isoprene

Isoprene was recovered from Feed Gas A (nitrogen carrier) having an isoprene concentration of about 1% by volume using the isoprene recovery apparatus illustrated in FIG. 1. As a result, liquid isoprene was recovered at a recovery rate of 93.3%. The isoprene concentration (average value) in the discharged gas was 7 ppm.

Isoprene was recovered from Feed Gas B (air carrier) having an isoprene concentration of about 1% by volume using the isoprene recovery apparatus illustrated in FIG. 1. As a result, liquid isoprene was recovered at a recovery rate of 92.1%. The isoprene concentration (average value) of the discharged gas was 7 ppm.

Isoprene was recovered from Feed Gas C (saturated water vapor-air carrier) having an isoprene concentration of about 1% by volume using the isoprene recovery apparatus illustrated in FIG. 1. As a result, liquid isoprene was recovered at a recovery rate of 82.7%. It was determined that the recovery rate of isoprene was significantly decreased when the moisture content in the feed gas was large. The isoprene concentration (average value) of the discharged gas was 7 ppm.

Isoprene was recovered from Feed Gas D (simulated fermented gas) having an isoprene concentration of about 1% by volume using the isoprene recovery apparatus illustrated in FIG. 2. As a result, liquid isoprene was recovered at a recovery rate of 98.1%. The isoprene concentration (average value) of the discharged gas was 2 ppm.

Isoprene was also recovered from Feed Gas D (simulated fermented gas) having an isoprene concentration of about 1% by volume using the isoprene recovery apparatus illustrated in FIG. 3. As a result, liquid isoprene was recovered at a recovery rate of 95.7%. The isoprene concentration (average value) of the discharged gas was 2 ppm.

Here, the "recovery rate of isoprene" means the ratio of the weight (WB) of the liquid isoprene recovered by the isoprene recovery apparatus to the weight (WA) of the regent isoprene used for preparing the feed gas, that is, 100×WB/WA (%).

The results are set forth in TABLE 4.

TABLE 4

| Recovery result of isoprene | | | | |
| --- | --- | --- | --- | --- |
| | Feed gas*[1] | Pretreatment | Recovery rate of isoprene (%) | Isoprene concentration of discharged gas (ppm) |
| A | Nitrogen carrier | — | 93.3 | 7 |
| B | Air carrier | — | 92.1 | 7 |
| C | Saturated water vapor-air carrier | — | 82.7 | 7 |
| D | Simulated fermented gas | Dehydration | 98.1 | 2 |
| D | Simulated fermented gas | Water washing and dehydration | 95.7 | 2 |

*[1]containing isoprene at a concentration of about 1% by volume

2.6. Quality Evaluation of Recovered Isoprene

A GC-MS analysis of the isoprene recovered in "2.5. Recovery results of isoprene" above was carried out. The GC-MS analysis was carried out using the HP-5MSUI column manufactured by Agilent Technologies, Inc., under conditions of an inlet temperature of 280° C. and a detector temperature of 250° C. The temperature of the column was maintained at 30° C. for 5 minutes and thereafter the temperature was raised at 25° C./min. After the temperature reached to 300° C., the temperature was maintained for 5 minutes.

The results of the GC-MS analysis are set forth in TABLE 5 to TABLE 9.

As a result, four components of 1-Propanol, 2-methyl (Retention Time (R.T.) 6:00), Acetoin (R.T.: 7:40), 1-Butanol, 3-methyl (R.T.: 8:04), and Pentane, 3-methyl (R.T.: 8:07), which were not detected in the isoprene recovered from Feed Gases A, B, and C, were detected in the isoprene recovered from Feed Gas D (pretreatment: dehydration) (TABLE 5 to TABLE 8). Acetoin and Pentane, 3-methyl were not detected in the isoprene recovered from Feed Gas D (pretreatment: water washing and dehydration). Therefore, it was determined that the organic impurities in the recovered isoprene could be reduced by organic substance removal treatment (TABLE 9).

TABLE 5

GC-MS analysis result of isoprene recovered from Feed Gas A (nitrogen carrier)

| R.T. | Peak intensity | Deduced compound |
|---|---|---|
| 1:22 | 140498 | Nitrogen oxide |
| 1:37 | 512772 | Methanol |
| 1:51 | 24532 | 2-Butene |
| 2:06 | 78247 | 2-Pentene |
| 2:16 | 8968 | Pentene |
| 2:33 | 242383 | Isopentene |
| 2:48 | 12231256 | Isoprene |
| 4:06 | 193589 | Isobutenal |
| 4:37 | 675366 | 2-Butenone |
| 5:29 | 83499 | Furan, 2-methyl- |
| 6:09 | 396061 | Isoprene oxide |
| 6:45 | 21921 | Benzene |
| 7:11 | 80646 | trans-2-Pentenal |
| 7:44 | 5499 | Furan, 2-(dichloromethyl)-tetrahydro- |
| 8:12 | 4822 | 2-Butenal, 2-methyl- |
| 8:34 | 19787 | 1,3,5-Cycloheptatriene |
| 9:16 | 14363 | 1-Heptan-4-ol |
| 9:18 | 23440 | Tetrahydro-2-furanmethanol |
| 9:28 | 18914 | 2-Butynoic acid, 4-[(tetrahydro-2H-pyran-2-yl)oxy], methyl |
| 9:37 | 57447 | Isobutenal |
| 9:48 | 107327 | 1-Methylcyclopropanecarboxylic acid |
| 10:02 | 84825 | Cyclobutane, 1,3-diisopropenyl-, trans |
| 10:21 | 53587 | Cyclobutane, 1,2-dicycropropyl- |
| 10:38 | 322581 | D-Limonene |
| 10:40 | 478165 | 1,5-Cyclooctadiene, 3,4-dimethyl |
| 10:57 | 66704 | trans-2-methyl-4-hexen-3-ol |
| 11:10 | 9710020 | Cyclohexene, 1-methyl-5-(1-methylethenyl)- |
| 11:13 | 2417621 | D-Limonene |
| 11:22 | 74724 | 2-Pentene-1-ol, 2-methyl |
| 11:36 | 128996 | 1,5-Cyclooctadiene, 1,6-dimethyl- |
| 11:56 | 288243 | Cyclopentene, 1,4-dimethyl-5-(1-methylethyl) |
| 11:59 | 688338 | Cycrohexene, 1-methyl-4-acetyl |

TABLE 6

GC-MS analysis result of isoprene recovered from Feed Gas B (air carrier)

| R.T. | Peak intensity | Deduced compound |
|---|---|---|
| 1:23 | 91898 | Nitrogen oxide |
| 1:38 | 39444 | Methanol |
| 1:52 | 7641 | 2-Butene |
| 2:07 | 49984 | 2-Pentene |
| 2:16 | 5326 | Pentene |
| 2:33 | 239226 | Isopentene |
| 2:49 | 12280294 | Isoprene |
| 4:07 | 135096 | Isobutenal |
| 4:37 | 461692 | 2-Butenone |
| 5:29 | 671520 | Furan, 2-methyl- |
| 6:09 | 228548 | Isoprene oxide |
| 6:46 | 27230 | Benzene |
| 7:11 | 195010 | trans-2-Pentenal |
| 7:44 | 8423 | Furan, 2-(dichloromethyl)-tetrahydro- |
| 8:12 | 137405 | 2-Butenal, 2-methyl- |
| 8:35 | 59891 | 1,3,5-Cycloheptatriene |
| 9:18 | 27244 | Tetrahydro-2-furanmethanol |
| 9:29 | 12275 | 2-Butynoic acid, 4-[(tetrahydro-2H-pyran-2-yl)oxy], methyl |
| 9:37 | 48571 | Isobutenal |
| 9:48 | 68215 | 1-Methylcyclopropanecarboxylic acid |
| 10:02 | 373491 | Cyclobutane, 1,3-diisopropenyl-, trans |
| 10:22 | 303668 | Cyclobutane, 1,2-dicycropropyl- |
| 10:40 | 2205213 | 1,5-Cyclooctadiene, 3,4-dimethyl |
| 10:57 | 60247 | trans-2-methyl-4-hexen-3-ol |
| 11:11 | 13099793 | Cyclohexene, 1-methyl-5-(1-methylethenyl)- |
| 11:22 | 64772 | 2-Pentene-1-ol, 2-methyl |
| 11:36 | 685796 | 1,5-Cyclooctadiene, 1,6-dimethyl- |
| 11:56 | 233728 | Cyclopentene, 1,4-dimethyl-5-(1-methylethyl) |
| 11:59 | 570419 | Cycrohexene, 1-methyl-4-acetyl |
| 14:13 | 1738007 | p-tert-Butyl catechol |

TABLE 7

GC-MS analysis result of isoprene recovered from Feed Gas C (saturated water vapor-air carrier)

| R.T. | Peak intensity | Deduced compound |
|---|---|---|
| 1:39 | 25125 | Methanol |
| 1:53 | 8378 | 2-Butene |
| 2:06 | 99574 | 2-Pentene |
| 2:16 | 6853 | Pentene |
| 2:33 | 330850 | Isopentene |
| 2:48 | 12602124 | Isoprene |
| 4:06 | 47267 | Isobutenal |
| 5:29 | 1354688 | Furan, 2-methyl- |
| 6:10 | 18286 | Isoprene oxide |
| 7:11 | 125916 | trans-2-Pentenal |
| 8:12 | 64331 | 2-Butenal, 2-methyl- |
| 8:35 | 6955 | 1,3,5-Cycloheptatriene |
| 10:02 | 48053 | Cyclobutane, 1,3-diisopropenyl-, trans |
| 10:22 | 35193 | Cyclobutane, 1,2-dicycropropyl- |
| 10:38 | 200959 | D-Limonene |
| 10:40 | 310816 | 1,5-Cyclooctadiene, 3,4-dimethyl |
| 11:10 | 676652 | Cyclohexene, 1-methyl-5-(1-methylethenyl)- |
| 11:13 | 1477230 | D-Limonene |
| 11:36 | 75986 | 1,5-Cyclooctadiene, 1,6-dimethyl- |
| 11:56 | 66240 | Cyclopentene, 1,4-dimethyl-5-(1-methylethyl) |
| 11:59 | 165558 | Cycrohexene, 1-methyl-4-acetyl |

TABLE 8

GC-MS analysis result of isoprene recovered from
Feed Gas D (simulated fermented gas; dehydration)

| R.T. | Peak intensity | Deduced compound |
|---|---|---|
| 1:38 | 10367 | Methanol |
| 1:52 | 7220 | 2-Butene |
| 2:05 | 134530 | 2-Pentene |
| 2:15 | 7575 | Pentene |
| 2:32 | 354072 | Isopentene |
| 2:47 | 11683900 | Isoprene |
| 4:05 | 42560 | Isobutenal |
| 4:38 | 7936 | 2-Butenone |
| 5:28 | 624521 | Furan, 2-methyl- |
| 6:00 | 140661 | 1-Propanol, 2-methyl |
| 6:09 | 23303 | Isoprene oxide |
| 7:11 | 36410 | trans-2-Pentenal |
| 7:40 | 20249 | Acetoin |
| 8:04 | 46400 | 1-Butanol, 3-methyl |
| 8:07 | 6272 | Pentane, 3-methyl |
| 8:12 | 163648 | 2-Butenal, 2-methyl- |
| 8:35 | 8882209 | 1,3,5-Cycloheptatriene |
| 10:02 | 30561 | Cyclobutane, 1,3-diisopropenyl-, trans |
| 10:21 | 18144 | Cyclobutane, 1,2-dicycropropyl- |
| 10:40 | 173105 | 1,5-Cyclooctadiene, 3,4-dimethyl |
| 11:10 | 2762309 | Cyclohexene, 1-methyl-5-(1-methylethenyl)- |
| 11:36 | 27342 | 1,5-Cyclooctadiene, 1,6-dimethyl- |
| 11:59 | 59392 | Cycrohexene, 1-methyl-4-acetyl |
| 14:13 | 8057 | p-tert-Butyl catechol |

TABLE 9

GC-MS analysis result of isoprene recovered from Feed Gas
D (simulated fermented gas; water washing and dehydration)

| R.T. | Peak intensity | Deduced compound |
|---|---|---|
| 1:39 | 11638 | Methanol |
| 1:53 | 6241 | 2-Butene |
| 2:06 | 88839 | 2-Pentene |
| 2:16 | 5571 | Pentene |
| 2:33 | 321739 | Isopentene |
| 2:48 | 12767373 | Isoprene |
| 4:06 | 31444 | Isobutenal |
| 4:40 | 5572 | 2-Butenone |
| 5:29 | 528026 | Furan, 2-methyl- |
| 6:01 | 58606 | 1-Propanol, 2-methyl |
| 6:10 | 9831 | Isoprene oxide |
| 7:11 | 18594 | trans-2-Pentenal |
| 8:04 | 16686 | 1-Butanol, 3-methyl |
| 8:12 | 14048 | 2-Butenal, 2-methyl- |
| 8:35 | 9469437 | 1,3,5-Cycloheptatriene |
| 10:02 | 21656 | Cyclobutane, 1,3-diisopropenyl-, trans |
| 10:22 | 10765 | Cyclobutane, 1,2-dicycropropyl- |
| 10:40 | 114953 | 1,5-Cyclooctadiene, 3,4-dimethyl |
| 11:10 | 1900754 | Cyclohexene, 1-methyl-5-(1-methylethenyl)- |
| 11:13 | 373484 | D-Limonene |
| 11:36 | 17474 | 1,5-Cyclooctadiene, 1,6-dimethyl- |
| 11:59 | 42151 | Cycrohexene, 1-methyl-4-acetyl |
| 14:13 | 22212 | p-tert-Butyl catechol |

Example 3

3. Recovery of Isoprene by PSA Method 3.1. Description of Isoprene Recovery Apparatus and Recovery Conditions In this Example, the isoprene recovery apparatus illustrated in FIG. 1 was used. A porous adsorbent layer of the hydrophobic molecular sieve "Hisiv-3000" was provided in both of the first adsorption tower 1 (inner diameter 3.5 cm) and the second adsorption tower 2 (inner diameter 3.5 cm). The porous adsorbent layer was pre-coated by blowing with gas having an isoprene concentration of 1% by volume.

In the adsorption step, the feed gas 3 prepared by adjusting the isoprene concentration to 1% by volume was supplied to the first adsorption tower 1 (or the second adsorption tower 2) through the feed gas supply pipes 10 and 11 (or 10 and 11'). Conditions at the time of adsorption were a temperature of 25° C., a pressure of 101.3 kPa, and a feed gas linear velocity of 1.0 cm/sec. The isoprene concentration of the discharged gas 5 emitted to the atmosphere after the adsorption step was measured with the sensor gas chromatograph ("ODSA-P2", manufactured by FIS Inc.).

In the desorption step, nitrogen gas served as the purge gas 4 and the pressure in the adsorption tower was reduced to 1.2 kPa with the vacuum pump 6 (linear velocity of purge gas: 8.8 cm/sec). Cooling water having a temperature of 10° C. was circulated in the condenser 7 to cool the purge gas containing isoprene.

The operation was carried out by alternately switching the adsorption step and the desorption step (the number of iterations of each step: 80 times; switching time of each step: 15 minutes).

3.2. Method for Preparing Feed Gas

Nitrogen gas was aerated into regent isoprene (manufactured by Tokyo Kasei Kogyo Co., Ltd.) that was cooled to −5° C. at a flow rate of 30 mL/min. The obtained gas was further diluted with 570 mL/min of nitrogen gas to obtain Feed Gas E (nitrogen gas carrier) containing isoprene in a concentration of about 1% by volume.

3.3. Recovery Result of Isoprene

Isoprene was recovered from Feed Gas E (nitrogen carrier) by the isoprene recovery apparatus illustrated in FIG. 1. As a result, liquid isoprene was recovered at a recovery rate of 85.5%. The isoprene concentration (average value) of the discharged gas was 4 ppm.

Example 4

Isoprene was recovered in the same manner as EXAMPLE 3 except that the pressure in the desorption step was changed to 3.3 kPa and the linear velocity of the purge gas at the time of the desorption step was changed to 0.96 cm/sec. As a result, liquid isoprene was recovered at a recovery rate of 36.6%. The isoprene concentration (average value) of the discharged gas was 0.51% by volume.

Example 5

5. Recovery of Isoprene from Fermented Gas Containing Isoprene Obtained by Culturing Microorganism having an Ability to Produce Isoprene 5.1. Description of Isoprene Recovery Apparatus and Recovery Conditions In this Example, the isoprene recovery apparatus illustrated in FIG. 2 was used. A porous adsorbent layer formed of the hydrophobic silica gel "S-6" was provided in both of the first adsorption tower 1 (inner diameter 3.5 cm) and the second adsorption tower 2 (inner diameter 3.5 cm). The porous adsorbent layer was pre-coated by blowing with gas having an isoprene concentration of 0.1% by volume.

In the adsorption step, the fermented gas generated from the fermentation tank was used as the feed gas 3. After the feed gas 3 was subjected to dehydration treatment and organic substance removal treatment, the treated feed gas 3, in an amount of 1/15 relative to the whole amount, was supplied to the first adsorption tower 1 (or the second adsorption tower 2) through the feed gas supply pipes 10 and 11 (or 10 and 11'). Conditions at the time of adsorption were a temperature of 25° C., a pressure of 101.3 kPa, and a feed gas linear velocity of 1.2 cm/sec. The isoprene concentration of the discharged gas emitted to the atmosphere after the adsorption step was measured with the sensor gas chromatograph ("ODSA-P2", manufactured by FIS Inc.). The remaining gas, in an amount of 14/15 relative to the whole amount, which was not supplied to the adsorption tower, was subjected to adsorption treatment with an activated carbon column.

In the desorption step, nitrogen gas was used as the purge gas and the pressure in the adsorption tower was reduced to 3.3 kPa with the vacuum pump (linear velocity of purge gas: 1.6 cm/sec). Cooling water having a temperature of 10° C. was circulated in the condenser to cool the purge gas containing isoprene.

The operation was carried out by alternately switching the adsorption step and the desorption step (the number of iterations of each step: 120 times; switching time of each step: 15 minutes).

5.2. Method for Preparing Fermented Gas

5.2.1. Culture Conditions for Microorganism having Ability to Produce Isoprene Isoprene-producing bacterium *Pantoea ananatis* (which may be abbreviated as "isoprene-producing bacterium *P. ananatis*") was used as the microorganism having an ability to produce isoprene. The isoprene-producing bacterium *Pantoea ananatis* strain was applied onto an LB plate containing 60 mg/L of chloramphenicol and the strain was cultured at 34° C. for 16 hours.

After 0.3 L of the glucose culture medium described in TABLE 3 was charged into each of two fermentation tanks having a volume of 1 L, the fully grown strain contained on one plate was inoculated and culture was started. As culture conditions, pH was controlled at 7.0 (controlled with ammonia) and stirring was carried out so that an oxygen concentration was controlled at 5% or more in the culture medium by aerating at 30° C. at 150 mL/min. In this Example, 0.15 L of the A part and the B part of the glucose culture medium described in TABLE 3 were prepared to provide the glucose culture medium.

When all of the glucose contained in the culture medium was consumed, 400 mL of the culture broth was charged into 20 L of a glucose culture medium described in TABLE 10 below in a fermentation tank having a volume of 50 L. As culture conditions, pH was controlled at 7.0 (controlled with ammonia) and stirring was carried out so that an oxygen concentration was controlled at 5% or more in the culture medium by aerating at 30° C. at 10 L/min. During the culture, glucose adjusted to have a concentration of 500 g/L was continuously added so that the glucose concentration of the culture medium was kept at 10 g/L or more. Finally, 3,884 g of glucose was consumed during the culture for 48 hours.

TABLE 10

| Glucose culture medium composition | |
|---|---|
| A part (final concentration) | |
| Glucose | 80 g/L |
| MgSO$_4$•7aq | 2.0 g/L |
| B part | |
| (NH$_4$)$_2$SO$_4$ | 2.0 g/L |
| KH$_2$PO$_4$ | 2.0 g/L |
| FeSO$_4$•7aq | 20 mg/L |
| MnSO$_4$•5aq | 20 mg/L |
| Yeast Extract | 4.0 g/L |

After each of the A part and the B part described in TABLE 10 above was prepared in an amount of 0.15 L, the parts were heated and sterilized at 115° C. for 10 minutes. After naturally cooling, the A part and the B part were mixed, and chloramphenicol (60 mg/L) was added. The mixture was used as a culture medium.

5.2.2. Method for Inducing to Isoprene Production Phase

The isoprene-producing bacterium *P. ananatis* strain used in this Example expresses the mevalonate pathway upstream gene under the arabinose inducible promoter and thus the isoprene production amount was significantly increased by the presence of L-arabinose (manufactured by Wako Pure Chemical Industries, Ltd.). In this Example, L-arabinose was added to the glucose culture medium described in TABLE 10 so that the final concentration of L-arabinose was 20 mM and whereby the isoprene production phase was induced.

5.2.3. Isoprene Concentration of Fermented Gas

Figure 4:
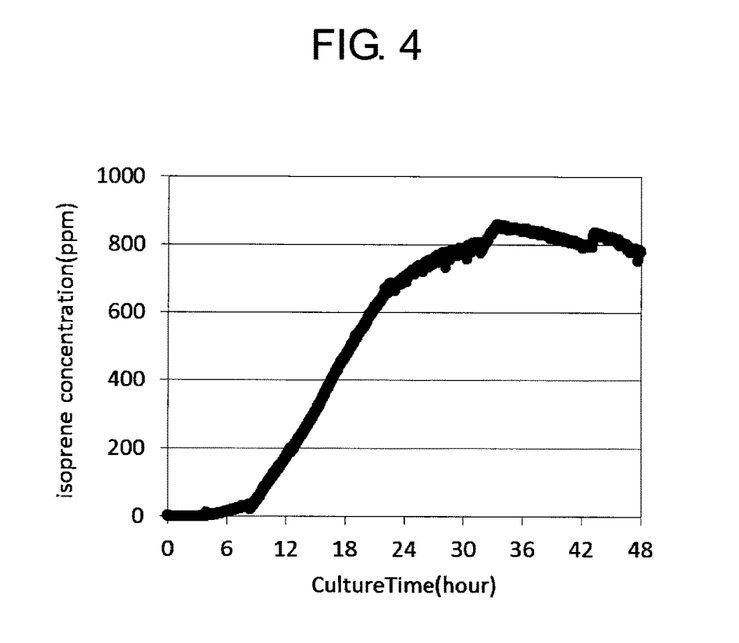
FIG. 4 is a graph illustrating an isoprene concentration of fermented gas obtained by culturing the isoprene-producing microorganism *P. ananatis* in EXAMPLE 5 described herein.

The isoprene concentration of the fermented gas was measured with a multi gas analyzer ("F10", manufactured by GASERA Ltd.). The results are shown in FIG. 4. Isoprene was detected after 6 hours from the start of the culture. The isoprene concentration of the fermented gas reached about 800 ppm after 30 hours from the start of the culture. Thereafter, the fermented gas containing isoprene at a concentration of about 800 ppm was supplied to the isoprene recovery apparatus until 48 hours after the start of the culture. At such time, the culture was terminated.

5.3. Method for Carrying out Dehydration Treatment and Organic Substance Removal Treatment of Fermented Gas The dehydration treatment and the organic substance removal treatment of the fermented gas were carried out by the following method. The fermented gas was cooled using a coil type heat exchanger (cooling water temperature: 10° C.) to condense moisture and organic substances. The condensed liquid was recovered with a gas-liquid separator.

5.4. Recovery Result of Isoprene

Isoprene was recovered from the fermented gas by the isoprene recovery apparatus illustrated in FIG. 2. As a result, liquid isoprene was recovered at a recovery rate of 81.5%. The isoprene concentration (average value) in the discharged gas was 7 ppm.

Figure 5:
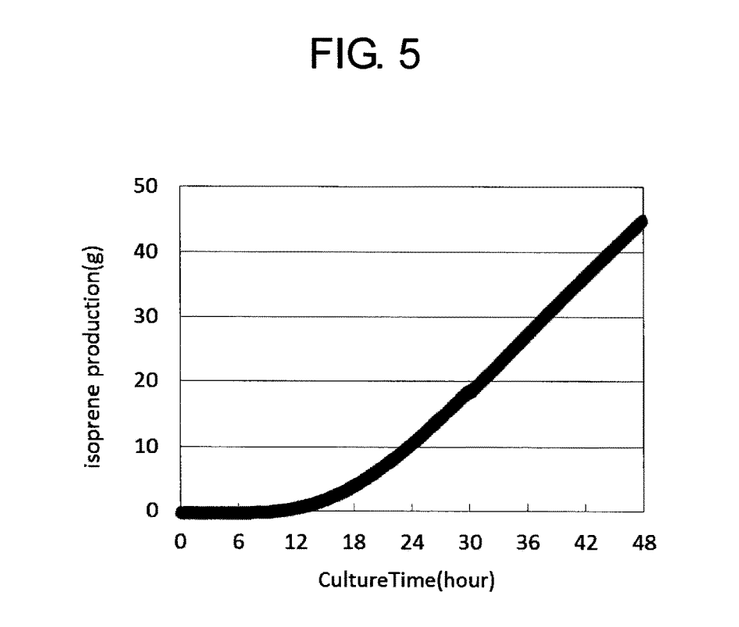
FIG. 5 is a graph illustrating a cumulative weight of isoprene in fermented gas obtained by culturing the isoprene-producing microorganism *P. ananatis* in EXAMPLE 5 described herein.

Here, in this Example, the "recovery rate of isoprene" means the ratio of the weight (WB) of liquid isoprene recovered by the isoprene recovery apparatus to the cumulative weight (WA') of the isoprene in the fermented gas supplied to the isoprene recovery apparatus, that is, 100× WB/WA' (%). The plot of the cumulative weight of isoprene contained in the fermented gas relative to the culture time is shown in FIG. 5.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method, comprising:
contacting a fermented gas comprising isoprene with a porous adsorbent; and
desorbing isoprene adsorbed on the porous adsorbent at a temperature of 80° C. or less;
wherein:
the fermented gas is obtained by culturing a microorganism having an ability to produce isoprene;
desorbing isoprene comprises desorbing isoprene gas; and
the porous adsorbent is a hydrophobidized silica gel with an average pore size of 60 Angstroms or less.

2. The method according to claim 1, comprising recovering liquid isoprene by cooling the desorbed isoprene.

3. The method according to claim 1, wherein the microorganism having an ability to produce isoprene is a bacterium of the genus *Pantoea*.

4. The method according to claim 1, wherein desorbing isoprene adsorbed on the porous adsorbent comprises desorbing at a temperature of 60° C. or less.

5. The method according to claim 1, comprising performing a pressure swing adsorption method.

6. The method according to claim 5, wherein:
contacting the fermented gas with the porous adsorbent comprises contacting at a pressure (PI-1);
desorbing isoprene adsorbed on the porous adsorbent comprises desorbing at a pressure (PI-2); and
the pressures PI-1 and PI-2 satisfy PI-1-PI-2>50 kPa.

7. The method according to claim 5, comprising, in sequence:
contacting the fermented gas with the porous adsorbent;
desorbing isoprene adsorbed on the porous adsorbent;
again contacting the fermented gas with the porous adsorbent; and
again desorbing isoprene adsorbed on the porous adsorbent.

8. The method according to claim 1, comprising dehydrating the fermented gas before contacting the fermented gas with the porous adsorbent.

9. The method according to claim 1, comprising removing an organic substance from the fermented gas before contacting the fermented gas with the porous adsorbent.

10. The method according to claim 1, further comprising, after contacting the fermented gas with the porous adsorbent, discharging fermented gas having an isoprene concentration of 0.8 C0 or less;
wherein C0 is an isoprene concentration of the fermented gas contacted with the porous adsorbent.

11. A method, comprising:
culturing a microorganism having an ability to produce isoprene to obtain a fermented gas comprising isoprene;
contacting the fermented gas comprising isoprene with a porous adsorbent; and
desorbing isoprene adsorbed on the porous adsorbent at a temperature of 80° C. or less;
wherein:
desorbing isoprene comprises desorbing isoprene gas, and
the porous adsorbent is a hydrophobidized silica gel with an average pore size of 60 Angstroms or less.

12. The method according to claim 11, comprising recovering liquid isoprene by cooling the desorbed isoprene.

13. The method according to claim 11, wherein the microorganism having an ability to produce isoprene is a bacterium of the genus *Pantoea*.

14. The method according to claim 11, wherein desorbing isoprene adsorbed on the porous adsorbent comprises desorbing at a temperature of 60° C. or less.

15. The method according to claim 11, comprising performing a pressure swing adsorption method.

16. The method according to claim 15, wherein:
contacting the fermented gas with the porous adsorbent comprises contacting at a pressure (PI-1);
desorbing isoprene adsorbed on the porous adsorbent comprises desorbing at a pressure (PI-2); and
the pressures PI-1 and PI-2 satisfy PI-1-PI-2>50 kPa.

17. The method according to claim 15, comprising, in sequence:
contacting the fermented gas with the porous adsorbent;
desorbing isoprene adsorbed on the porous adsorbent;
again contacting the fermented gas with the porous adsorbent; and
again desorbing isoprene adsorbed on the porous adsorbent.

18. The method according to claim 11, comprising dehydrating the fermented gas before contacting the fermented gas with the porous adsorbent.

19. The method according to claim 11, comprising removing an organic substance from the fermented gas before contacting the fermented gas with the porous adsorbent.

20. The method according to claim 11, further comprising, after contacting the fermented gas with the porous adsorbent, discharging fermented gas having an isoprene concentration of 0.8 C0 or less;
wherein C0 is an isoprene concentration of the fermented gas contacted with the porous adsorbent.

* * * * *